US012691041B2

(12) United States Patent
Moszner et al.

(10) Patent No.: US 12,691,041 B2
(45) Date of Patent: Jul. 28, 2026

(54) SELF-ADHESIVE DENTAL COMPOSITE CEMENT WITH GOOD TRANSPARENCY

(71) Applicant: Ivoclar Vivadent AG, Schaan (LI)

(72) Inventors: Norbert Moszner, Triesen (LI); Alexandros Gianasmidis, Balgach (CH); Delphine Catel, Rans (CH); Yohann Catel, Rans (CH); Andy Brot, Balzers (LI); Tim Haldner, Mauren (LI); Thorsten Bock, Feldkirch (AT); Barbara Grabenbauer, Rebstein (CH)

(73) Assignee: Ivoclar Vivadent AG, Schaan (LI)

(*) Notice: Subject to any disclaimer, the term of this patent is extended or adjusted under 35 U.S.C. 154(b) by 770 days.

(21) Appl. No.: 18/147,687

(22) Filed: Dec. 28, 2022

(65) Prior Publication Data

US 2023/0201082 A1 Jun. 29, 2023

(30) Foreign Application Priority Data

Dec. 29, 2021 (EP) .................................... 21218203

(51) Int. Cl.

| | |
|---|---|
| ***A61K 6/889*** | (2020.01) |
| ***A61C 5/30*** | (2017.01) |
| ***A61C 5/70*** | (2017.01) |
| ***A61K 6/17*** | (2020.01) |
| ***A61K 6/61*** | (2020.01) |
| ***A61K 6/76*** | (2020.01) |
| ***A61K 6/77*** | (2020.01) |

(52) U.S. Cl.

CPC ................ *A61K 6/889* (2020.01); *A61C 5/30* (2017.02); *A61C 5/70* (2017.02); *A61K 6/17* (2020.01); *A61K 6/61* (2020.01); *A61K 6/76* (2020.01); *A61K 6/77* (2020.01)

(58) Field of Classification Search

CPC ...................................................... A61K 6/889

See application file for complete search history.

(56) References Cited

U.S. PATENT DOCUMENTS

| | | | | |
|---|---|---|---|---|
| 7,932,304 | B2 | 4/2011 | Moszner et al. | |
| 8,129,444 | B2 * | 3/2012 | Hecht ........................ | C09J 4/00 106/35 |
| 8,648,062 | B2 | 2/2014 | Haapasalo | |
| 10,064,789 | B2 | 9/2018 | Matsumoto et al. | |
| 11,357,709 | B2 | 6/2022 | Moszner et al. | |
| 2004/0048226 | A1 | 3/2004 | Garman | |

(Continued)

FOREIGN PATENT DOCUMENTS

| | | | |
|---|---|---|---|
| DE | 102005022172 | A1 | 11/2006 |
| EP | 4094748 | A1 | 11/2022 |

(Continued)

OTHER PUBLICATIONS

EDTA Product Specification; Sigma-Aldrich; no date.*

(Continued)

*Primary Examiner* — Michael F Pepitone

(74) *Attorney, Agent, or Firm* — Ann M. Knab; Thad McMurray

(57) ABSTRACT

A radically polymerizable composition having at least one acidic radically polymerizable monomer, at least one fluoroaluminosilicate glass filler and/or radiopaque glass filler, and at least one masking agent in solid form.

17 Claims, 1 Drawing Sheet

(56) References Cited

U.S. PATENT DOCUMENTS

| | | | | |
|---|---|---|---|---|
| 2007/0040151 | A1 | 2/2007 | Utterodt et al. | |
| 2009/0139433 | A1 | 6/2009 | Moszner et al. | |
| 2014/0294742 | A1 | 10/2014 | Fischer et al. | |
| 2021/0161770 | A1 * | 6/2021 | Bottcher | A61K 6/838 |
| 2021/0189098 | A1 | 6/2021 | Hara et al. | |

FOREIGN PATENT DOCUMENTS

| | | | | |
|---|---|---|---|---|
| JP | H1160428 | A | | 3/1999 |
| JP | 2004051554 | A | * | 2/2004 |
| JP | 2021031409 | A | | 3/2021 |
| JP | 2021100919 | A | | 7/2021 |

OTHER PUBLICATIONS

Ethylenediaminetetraacetate sodium salt Product Specification; Sigma-Aldrich; no date.*

Yoshihara, K., et al., Silane-coupling effect of a silane-containing self-adhesive composite cement, Dental Materials, Jul. 2020, vol. 36, No. 7, pp. 914-926. Jul. 2020.

* cited by examiner weeks at room temperature

■ Composite paste without EDTA
● Composite paste with 1.26% EDTA
▼ Composite paste with 3.66% EDTA weeks at room temperature ■ Composite cement without EDTA
● Composite cement with 1.03% EDTA
▼ Composite cement with 3.08% EDTA

SELF-ADHESIVE DENTAL COMPOSITE CEMENT WITH GOOD TRANSPARENCY

CROSS-REFERENCE TO RELATED APPLICATIONS

This application claims priority to European Patent Application No. 21218203.4 filed on Dec. 29, 2021, the disclosure of which is incorporated herein by reference in its entirety.

TECHNICAL FIELD

The present invention relates to radically polymerizable, self-adhesive composites with improved transparency, which are particularly suitable as dental materials, e. g. as dental cements, filling composites, or veneering materials as well as for the fabrication of inlays, onlays, or crowns.

BACKGROUND

Composites are mainly used in the dental field for the fabrication of direct and indirect fillings, i. e. as direct and indirect filling composites and as cements. The polymerizable organic matrix of the composites usually consists of a mixture of monomers, initiator components, and stabilizers. Mixtures of dimethacrylates are usually used as monomers, which may also contain monofunctional and functionalized monomers. Commonly used dimethacrylates are 2,2-bis[4-(2-hydroxy-3-methacryloy-loxypropyl)phenyl]propane (bis-GMA), 1,6-bis[2-methacryloyloxyethoxycarbonylamino]-2-trimethylhexane,2,4 (UDMA), which have high viscosity and produce polymers with very good mechanical properties and low polymerization shrinkage. Triethylene glycol dimethacrylate (TEGDMA), 1,10-decanediol dimethacrylate ($D_3MA$) or bis(3-methacryloyloxymethyl)tricyclo-[5.2.1.$0^{2,6}$]decane (DCP) are mainly used as reactive diluents. Monofunctional methacrylates, such as p-cumylphen-oxyethylene glycol methacrylate (CMP-1E), are also suitable for reducing viscosity and additionally cause a reduction in network density and increased double-bond conversion.

To produce self-adhesive composites, strongly acidic adhesive monomers are used, such as 10-methacryloyloxydecyl dihydrogen phosphate (MDP), which etches the tooth structure and leads to adhesion to enamel/dentin by ionic relationship. Adhesive monomers impart self-adhesive properties to composites and thus enable the composites to be used without pretreatment of the tooth structure with an enamel/dentin adhesive, which makes their use particularly attractive.

In addition to the organic matrix, composites contain one or more fillers, which are usually surface-modified with a polymerizable coupling agent, such as 3-methacry-loyloxypropyltrimethoxysilane. Fillers improve the mechanical properties (strength, modulus of elasticity, abrasion resistance) and the processing properties (paste consistency, stuffability) of the materials and impart radiopacity.

It is problematic that acidic adhesive monomers often interact adversely with fillers. For example, the acidic adhesion monomers are bound to the surface of the fillers by the formation of insoluble salts, or they form poorly soluble salts during storage with ions released from the fillers. This leads to a significant reduction of the adhesion monomer concentration in the resin matrix, which is associated with a reduction or even a loss of the adhesive properties of the cement. Composites with acidic adhesive monomers therefore have only limited storage stability.

Methacrylate-based dental materials are cured by radical polymerization, using radical photoinitiators, thermal initiators, or redox initiator systems, depending on the field of application. Dual-curing systems contain a combination of photoinitiators and redox initiators.

Composite cements usually contain redox systems because they ensure sufficient curing even when light curing is not possible due to insufficient transmittance. Redox initiator systems based on a mixture of dibenzoyl peroxide (DBPO) with tertiary aromatic amines, such as N,N-diethanol-p-toluidine (DEPT), N,N-dimethyl-sym.-xylidine (DMSX) or N,N-diethyl-3,5-di-tert-butylaniline (DABA), are usually used. Since radical formation in DBPO/amine-based redox initiator systems is greatly impaired by strong acids and thus also by strongly acidic adhesive monomers, cumene hydroper-oxide-containing redox initiator systems in combination with thioureas, such as ace-tylthiourea, are preferred.

In order to ensure sufficient storage stability of the redox initiators, redox initiator system-based materials are usually used as so-called 2-component systems (2C), whereby the oxidizing agent (peroxide or hydroperoxide) and the reducing agent (amines, sulfinic acids, barbiturates, thioureas, etc.) are incorporated into separate components. These are mixed together just before use. For mixing, mainly double-push syringes are used, which have separate cylindrical chambers to hold the components. The components are pushed out of the chambers simultaneously by two interconnected pistons and mixed together in a nozzle. To obtain mixtures that are as homogeneous as possible, it is advantageous to mix the components together in approximately equal volume proportions.

Conventional luting cements, such as ZnO eugenol cements, zinc phosphate cements, glass ionomer cements (GIC) and resin-modified glass ionomer cements (RMGI), are not suitable for use with double-push syringes because they contain a powder component, which makes mixing the components considerably more difficult. In addition, glass ionomer cements only have low transparency and relatively poor mechanical properties.

Conventional glass ionomer cements (GIC) contain an aqueous solution of a high molecular weight polyacrylic acid (PAA, number average molar mass greater than 30,000 g/mol) or a copolymer of comparable molar mass of acrylic acid and itaconic acid as liquid component and a calcium fluorine aluminum glass as powder component. After mixing the components, they cure by purely ionic ionomer formation. The disadvantages of glass ionomer cements are their low transparency and poor mechanical properties.

Resin-modified glass ionomer cements (RMGI) additionally contain hydrophilic monomers, such as 2-hydroxyethyl methacrylate (HEMA). They cure both by an acid-base reaction and by radical polymerization. Compared to conventional GIC, they are characterized by improved flexural strength.

US 2004/0048226A1, which is hereby incorporated by reference in its entirety, discloses a method for root canal treatment using a liquid containing EDTA as a cleaning and sterilizing solution.

U.S. Pat. No. 8,648,062 B2, which is hereby incorporated by reference in its entirety, discloses an EDTA-containing composition for irrigation of prepared dental root canals. The composition is said to enable simultaneous removal of the smear layer as well as disinfection.

US 2014/0294742 A1, which is hereby incorporated by reference in its entirety, describes solutions containing peroxide for the treatment of dental plaque, which may contain EDTA or an EDTA salt as a stabilizer.

JPH1160428 A discloses a dental adhesive containing an aqueous acid solution for pre-treating the tooth surface. Suitable acids are EDTA, phosphoric acid, and citric acid.

EP 3 045 160 A1 and corresponding U.S. Pat. No. 10,064,789 B2, which US patent is hereby incorporated by reference in its entirety, relate to dental composites based on (meth)acrylate monomers and filler, which contain a barbiturate in combination with a peroxide compound as initiator for the radical polymerization. The composites additionally contain aminocarboxylic acid chelating agents, such as EDTA or salts thereof, which are said to prevent a reaction of the barbiturate with metal ions and thus improve the storage stability of the materials.

DE 10 2005 022 172 A1 discloses polymerizable EDTA derivatives in which EDTA is covalently linked to ethylenically unsaturated monomers. The EDTA derivatives are immobilized during polymerization by integration into the organic matrix of dental materials and are said to improve the adhesion of dental adhesives to teeth.

EP 2 065 363 A1 and corresponding US 2009139433 A1, which US published application is hereby incorporated by reference in its entirety, discloses dental materials based on hydrolysis-stable alkylenediamine-N,N,N',N'-tetraacetic acid (meth)acrylamides, which exhibit good water solubility and improve the adhesion of the materials to enamel and dentin.

SUMMARY

It is an object of the present invention to provide storage-stable, self-adhesive dental composites with good transparency and good mechanical properties, which can be mixed and applied well as 2-component systems using double-push syringes. The composites should be particularly suitable as dental luting cements.

BRIEF DESCRIPTION OF THE DRAWINGS

Further details, advantages and features will be apparent from the following description of several exemplary embodiments of the invention with reference to the drawings, in which.

DETAILED DESCRIPTION

Figure 1:
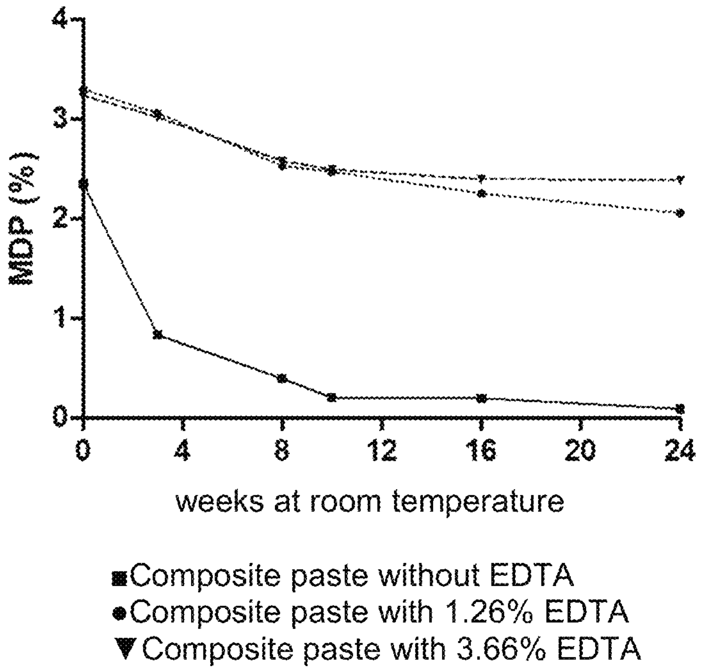
FIG. 1 shows a decrease in concentration of an acidic monomer MDP as a function of storage time in composite pastes with (▼; ●) and without (■) EDTA.

This problem is solved by filler-containing, radically polymerizable compositions comprising at least one acidic, radically polymerizable monomer, at least one fluoroaluminosilicate glass filler and/or radiopaque glass filler, and at least one solid masking agent. It was surprisingly found that masking agents, which are at least partially present in undissolved form, provide a significant increase in the storage stability of compositions containing acidic monomers and at least one fluoroaluminosilicate glass filler and/or radiopaque glass filler.

Masking agents preferred according to the invention are ethylenediaminetetraacetic acid (EDTA) and its disodium salt (disodium ethylenediaminetetraacetate), nitrilotri-acetic acid, diethylenetriaminepentaacetic acid, tetrasodium iminodisuccinate, and the trisodium salt of methylglycinediacetic acid. EDTA is particularly preferred.

The one or more masking agents are preferably added in a total amount of 0.5 to 6.0 wt. %, more preferably 0.7 to 5 wt. %, and most preferably 1.0 to 4.0 wt. %. All percentages herein refer to the total mass of the composition, unless otherwise stated.

The one or more masking agents are preferably used in particulate form and then practically behave like a filler, which is advantageous with regard to the mechanical properties. Particles preferably have an average size (D50 value) of 300 to 350 μm, more preferably of 200 to 250 μm, and most preferably of 100 to 170 μm. According to a particularly preferred embodiment of the invention, the D10 value of the particles is in a range from 130 to 150 μm, more preferably from 80 to 100 μm, and most preferably from 70 to 55 μm. The D50 value indicates the average particle size. D50 means that 50% of the particles are smaller than the specified value. Another important parameter is the D10 value as a measure of the smallest particles. D10 means that 10% of the particles are smaller than the specified value.

Unless otherwise stated, all particle sizes herein are volume-averaged particle sizes (D50 values), i.e. 50% of the total volume of all particles is contained in particles with a diameter smaller than the specified value. The D10 values also refer to the volu-metric diameter.

Particle size determination in the range from 0.1 μm to 1000 μm is preferably carried out by means of static light scattering (SLS), e. g. with an LA-960 static laser scattering particle size analyzer (Horiba, Japan) or with a Microtrac S100 particle size analyzer (Microtrac, USA). Here, a laser diode with a wavelength of 655 nm and an LED with a wavelength of 405 nm are used as light sources. The use of two light sources with different wavelengths enables the measurement of the entire particle size distribution of a sample in only one measurement run, whereby the measurement is carried out as a wet measurement. For this purpose, an aqueous dispersion of the filler is prepared and its scattered light is measured in a flow cell. The scattered light ana-lysis for calculating particle size and particle size distribution is carried out according to the Mie theory according to DIN/ISO 13320. The measurement of the particle size in a range from 1 nm to 0.1 μm is preferably carried out by dynamic light scattering (DLS) of aqueous particle dispersions, preferably with a He—Ne laser with a wavelength of 633 nm, at a scattering angle of 90° and at 25° C., e. g. with a Malvern Zetasizer Nano ZS (Malvern Instruments, Malvern UK).

In the case of aggregated and agglomerated particles, the primary particle size can be determined from TEM images. Transmission electron microscopy (TEM) is preferably performed using a Philips CM30 TEM at an accelerating voltage of 300 kV. For sample preparation, drops of the particle dispersion are applied to a 50 Å thick copper grid (mesh size of 300 mesh) coated with carbon, followed by evaporation of the solvent. The particles are counted and the arithmetic mean is calculated.

The compositions according to the invention contain at least one radically polymerizable monomer, preferably one or more mono- and/or polyfunctional monomers. Polyfunctional monomers are understood to be compounds with two or more, preferably 2 to 4 and in particular 2 radically polymerizable groups. Monofunctional monomers accordingly have only one radically polymerizable group. Polyfunctional monomers have crosslinking properties and are therefore also referred to as crosslinking monomers.

Preferred radically polymerizable groups are (meth)acrylate, (meth)ac-rylamide and vinyl groups.

According to the invention, a distinction is made between monomers containing acid groups and monomers which do not contain acid groups. The compositions according to the invention contain at least one monomer without acid groups and at least one monomer and/or oligomer with acid groups. The compositions according to the invention preferably comprise monomers with and monomers without acid groups in a weight ratio of from 1:5 to 1:36, more preferably from 1:6 to 1:25, and most preferably from 1:7 to 1:20.

ethyl)tricyclo-[5.2.1.0$^{2,6}$]decane (DCP), polyethylene glycol or polypropylene glycol dimethacrylates, such as polyethylene glycol 200-dimethacrylate or polyethylene glycol 400-dimethacrylate (PEG-200- or PEG-400-DMA) or 1,12-dodecanediol dimethacrylate. Bis-GMA, UDMA, V-380, triethylene glycol dimethacrylate (TEGDMA) and PEG-400-DMA (NK ester 9G) are particularly preferred.

The monomers tetramethylxylylene diurethane ethylene glycol di(meth)acrylate and tetramethylxylylene diurethane 2-methylethylene glycol di(meth)acrylate (V380), respectively, have the following formula:

V380

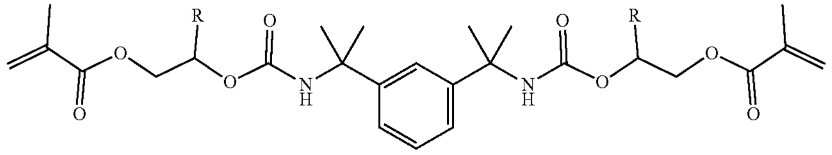

(R = H, $CH_3$)

Monomers without Acid Group

Preferred are compositions comprising at least one (meth) acrylate, more preferably at least one monofunctional or polyfunctional methacrylate, and most preferably at least one monofunctional or difunctional methacrylate or a mixture thereof.

Preferred monofunctional (meth)acrylates are benzyl, tetrahydrofurfuryl or isobornyl (meth)acrylate, p-cumyl phenoxyethylene glycol methacrylate (CMP-1E) and 2-([1,1'-biphenyl]-2-oxy)ethyl methacrylate (MA-836), tricyclodecane methyl (meth)acrylate, 2-(2-biphenyloxy) ethyl (meth)acrylate. CMP-1E and MA-836 are particularly preferred.

According to one embodiment, the compositions according to the invention preferably comprise at least one functionalized monofunctional (meth)acrylate. Functionalized monomers are understood to be those monomers which, in addition to at least one radically polymerizable group, carry at least one functional group, preferably a hydroxyl group. Preferred functionalized mono(meth)acrylates are 2-hydroxyethyl and hydroxyethyl propyl(methacrylate) and 2-acetoxyethyl methacrylate. Hydroxyethyl methacrylate is particularly preferred. The monomers containing acid groups mentioned below are not functionalized monomers within the meaning of the invention.

Preferred di- and polyfunctional (meth)acrylates are bisphenol-A-dimethacrylate, bis-GMA (an addition product of methacrylic acid and bisphenol-A-diglycidyl ether), ethoxy- or propoxylated bisphenol-A-dimethacrylates, such as the bisphenol A dimethacrylate SR-348c (Sartomer) with 3 ethoxy groups or 2,2-bis[4-(2-methacryloy-loxypropoxy) phenyl]propane, urethanes of 2-(hydroxymethyl)acrylic acid methyl ester and diisocyanates, such as 2,2,4-trimethylhexamethylene diisocyanate or isophorone diisocyanate, UDMA (an addition product of 2-hydroxyethyl methacrylate- and 2,2,4-trimethylhexamethylene-1,6-diisocyanate), tetramethylxylylene diurethane ethylene di(meth)acrylate or tetramethylxylylene diurethane-2-methylethylene glycol di(meth)acrylate (V380), di-, tri- or tetraethylene glycol dimethacrylate, trimethylolpropane trimethacrylate, pentaerythritol tetramethacrylate as well as glycerol di- and -trimethacrylate, 1,4-butanediol dimethacrylate, 1,10-decanediol dimethacrylate ($D_3MA$), bis(methacryloyloxym- In the above formula, the radicals R are independently H or $CH_3$, and the radicals may have the same meaning or different meanings. Preferably, a mixture is used that contains molecules in which both radicals are H, molecules in which both radicals are $CH_3$, and molecules in which one radical is H and the other radical is $CH_3$, with a ratio of H to $CH_3$ of 7:3 being preferred. Such a mixture is obtainable, for example, by reacting 1,3-bis(1-isocyanato-1-methylethyl)benzene with 2-hydroxypropyl methacrylate and 2-hydroxyethyl methacrylate.

Other preferred difunctional monomers include radically polymerizable pyrrolidones, such as 1,6-bis(3-vinyl-2-pyrrolidonyl)-hexane, or commercially available bisacrylamides such as methylene or ethylene bisacrylamide, as well as bis(meth)acrylamides, such as N,N'-diethyl-1,3-bis(acrylamido)propane, 1,3-bis(methacrylamido-) propane, 1,4-bis (acrylamido)butane or 1,4-bis(acryloyl)piperazine, which can be synthesized from the corresponding diamines by reaction with (meth)acrylic acid chloride. N,N'-diethyl-1,3-bis(acrylamido)propane (V-392) is particularly preferred. These monomers are characterized by high hydrolytic stability.

Monomers and Oligomers Containing Acid Groups

The compositions according to the invention contain at least one acidic radically polymerizable monomer and/or at least one acidic oligomer. Acidic monomers and oligomers are understood to mean monomers and oligomers, respectively, which contain at least one acid group, preferably a phosphoric acid ester, phosphonic acid or carboxy group, with phosphoric acid esters being particularly preferred. Acidic monomers and oligomers are also herein referred to as adhesive components or adhesive monomers or adhesive oligomers.

Preferred monomers containing acid groups are phosphoric ester and phosphonic acid monomers. Particularly preferred are 2-methacryloyloxyethylphenyl hydrogen phosphate, 10-methacryloyloxydecyl dihydrogen phosphate (MDP) glycerol dimethacrylate dihydrogen phosphate or dipentaerythritol pentamethacryloyloxy phosphate. 4-Vinylbenzylphosphonic acid, 2-[4-(dihydroxyphosphoryl)-2-oxa-butyl]-acrylic acid or hydrolysis-stable esters, such as 2-[4-(dihydroxyphosphoryl)-2-oxa-butyl]-acrylic acid 2,4,6-trimethylphenyl ester. MDP, 2-methacryloyloxyethylphenyl hydrogen phosphate and glycerol dimethacrylate dihydrogen phosphate are particularly preferred.

Other preferred monomers containing acid groups are COOH group-containing polymerizable monomers. Particularly preferred are 4-(meth)acryloyloxyethyltrimellitic anhydride, 10-methacryloyloxydecylmalonic acid, N-(2-hydroxy-3-methacryloyloxyp-ropyl)-N-phenylglycine and 4-vinylbenzoic acid.

Oligomers are understood to be polymers with a degree of polymerization $P_n$ of 2 to 100 ($P_n=M_n/M_u$; $M_n$: number average polymer molecular weight, $M_u$: molecular weight of the monomer unit). Acidic radically polymerizable oligomers have at least one acid group, preferably a carboxyl group, and at least one radically polymerizable group, preferably at least one (meth)acrylate group and in particular at least one methacrylate group.

Oligomers containing acid groups that are preferred according to the invention are oligomeric carboxylic acids, such as polyacrylic acid, preferably with a number average molecular weight $M_n$ of less than 7,200 g/mol, more preferably less than 7,000 g/mol and most preferably less than 6,800 g/mol, wherein $M_n$ is preferably in a range from 800 to 7,200 g/mol, particularly preferably from 500 to 7000 g/mol and most preferably from 500 to 6,800 g/mol. Oligomeric carboxylic acids with (meth)acrylate groups are particularly preferred. These can be obtained, for example, by reacting oligomeric polyacrylic acid with glycidyl methacrylate or 2-isocyanatoethyl methacrylate.

Unless otherwise stated, the molar mass of oligomers and polymers herein is the number-average molar mass, the absolute values of which can be determined by the known methods of freezing point depression (cryoscopy), boiling point elevation (ebullioscopy) or through the depression of the vapor pressure (vapor pressure osmo-metry). Preferably, the number average molecular weight of oligomers and polymers is determined by gel permeation chromatography (GPC). This is a relative method in which molecules are separated on the basis of their size, more precisely on the basis of their hydrodynamic volume. The absolute molar mass is determined by calibration with known standards.

The compositions according to the invention preferably also contain water. It has been found that a water content of 1 to 7 wt. %, particularly preferably 1 to 5% by weight, in each case based on the total mass of the composition, results in an improvement of the bonding effect to dentin and enamel, but does not lead to a complete dissolution of the masking agent.

The compositions according to the invention further comprise at least one initiator for initiating the radical polymerization, preferably a photoinitiator. Preferred photoinitiators are benzophenone, benzoin and derivatives thereof, α-diketones or derivatives thereof, such as 9,10-phenanthrenequinone, 1-phenyl-propane-1,2-dione, diacetyl and 4,4'-dichlorobenzil. Particularly preferred are camphorquinone (CC) and 2,2-di-methoxy-2-phenyl-acetophenone and, most preferably, α-diketones are used in combination with amines as reducing agents, such as 4-(dimethylamino)benzoic acid ethyl ester (EDMAB), N,N-dimethylaminoethyl methacrylate, N,N-dimethyl-sym.-xylidine or triethanolamine. Further preferred are Norrish type I photoinitiators, especially acyl or bisacyl phosphine oxides and most preferably monoacyltrialkylgerma-nium, diacyldialkylgermanium and tetraacylgermanium compounds, such as e. g. benzoyltrimethylgerman, dibenzoyldiethylgerman, bis(4-methoxybenzoyl)-diethylger-man (Ivocerin®), tetrabenzoylgerman or tetrakis(o-methylbenzoyl)german. Mixtures of the various photoinitiators can also be used, such as bis(4-methoxybenzoyl)diet-hylgerman or tetrakis(o-methylbenzoyl)german in combination with camphorquinone and 4-(dimethylamino) benzoic acid ethyl ester.

Further preferred are compositions containing a redox initiator for initiating radical polymerization, preferably a redox initiator based on an oxidizing agent and a reducing agent. Preferred oxidizing agents are peroxides and hydroperoxides in particular. A particularly preferred peroxide is benzoyl peroxide. Preferred hydroperoxides are the low-odor cumene hydroperoxide derivatives disclosed in EP 3 692 976 A1 and corresponding U.S. Pat. No. 11,357,709 B2, which US patent is hereby incorporated by reference in its entirety, the oligomeric CHP derivatives disclosed in EP 21315089.9, and, in particular, 4-(2-hydroperoxypropan-2-yl)phenylpropionate and cumene hydroperoxide (CHP).

Preferred reducing agents for combination with peroxides are tertiary amines, such as N,N-dimethyl-p-toluidine, N,N-dihydroxyethyl-p-toluidine, p-dimethylaminobenzoic acid ethyl ester or other aromatic dialkylamines, ascorbic acid, sulfinic acids, thiols and/or hydrogen silanes.

Preferred reducing agents for combination with hydroperoxides are thiourea derivatives, in particular the compounds listed in paragraph [0009] of EP 1 754 465 A1. Particularly preferred are methyl-, ethyl-, allyl-, butyl-, hexyl-, octyl-, benzyl-, 1,1,3-trime-thyl-, 1,1-diallyl-, 1,3-diallyl-, 1-(2-pyridyl-2-thiourea, acetyl-, propanoyl-, butanoyl-, pentanoyl-, hexanoyl-, heptanoyl-, octanoyl-, nonanoyl-, decanoyl-, benzoylthiourea and mixtures thereof. Quite particularly preferred are acetyl-, allyl-, pyridyl- and phe-nylthiourea as well as hexanoylthiourea and mixtures thereof as well as polymerizable thiourea derivatives, such as N-(2-methacryloyloxyethoxysuccinoyl)-thiourea and N-(4-vinylbenzoyl)-thiourea). In addition, a combination of one or more of said thiourea derivatives with one or more imidazoles may advantageously be used. Preferred imidazoles are 2-mercapto-1-methylimidazole or 2-mercaptobenzimida-zole.

In addition to at least one hydroperoxide and at least one thiourea derivative, the compositions according to the invention may further comprise at least one transition metal compound for accelerating curing. Transition metal compounds suitable according to the invention are in particular compounds derived from transition metals with at least two stable oxidation states. Particularly preferred are compounds of the elements copper, iron, cobalt, nickel, and manganese. These metals have the following stable oxidation states: Cu(I)/Cu(II), Fe(II)/Fe(III), Co(II)/Co(III), Ni(II)/Ni(III), Mn(II)/Mn(III). Compositions containing at least one copper compound are particularly preferred. The transition metal compounds are preferably used in catalytic amounts, particularly preferably in an amount of 10 to 200 ppm. These amounts do not lead to discoloration of the dental materials. Because of their good monomer solubility, the transition metals are preferably used in the form of their acetylacetonates, 2-ethylhexanoates or THF adducts. Further preferred are their complexes with poly-dentate ligands such as 2-(2-aminoethylamino)ethanol, triethylenetetramine, dime-thylglyoxime, 8-hydroxyquinoline, 2,2'-bipyridine or 1,10-phenanthroline. A particularly suitable initiator according to the invention is a mixture of cumene hydroperoxide (CHP) with at least one of the above-mentioned thiourea derivatives and copper(II) acetylacetonate. According to the invention, compositions which do not contain vanadium compounds are preferred.

The compositions according to the invention preferably do not contain barbituric acid or barbituric acid derivatives such as 1,3,5-trimethylbarbituric acid, 1-benzyl-5-phenylbarbituric acid, 5-butylbarbituric acid or 1-cyclohexyl-5-ethylbarbituric acid. Compositions containing barbiturates have unsatisfactory storage stability because barbiturates form polymerization-initiating radicals by oxidation with atmospheric oxygen. In addition, barbiturates have adverse physiological effects such as bradycardia, hypotension, or blood disorders.

The compositions according to the invention contain at least one inorganic filler. Compositions containing fillers are referred to as composites. Preferred are compositions containing at least one fluoroaluminosilicate glass filler (FAS filler) and/or a radiopaque glass filler.

Preferred radiopaque glass fillers have the following composition (wt. %): $SiO_2$: 20-80; $B_2O_3$: 2-15, BaO or SrO: 0-40; $Al_2O_3$: 2-20; CaO and/or MgO: 0-20; $Na_2O$, $K_2O$, $Cs_2O$: 0-10 each; $WO_3$: 0-20; ZnO: 0-20; $La_2O_3$: 0-10; $ZrO_2$: 0-15; $P_2O_5$: 0-30; $Ta_2O_5$, $Nb_2O_5$ or $Yb_2O_3$: 0-5; and $CaF_2$ and/or $SrF_2$ 0-10. Particularly preferred are radiopaque glass fillers with the following composition (wt. %): $SiO_2$: 50-75; $B_2O_3$: 2-15; BaO or SrO: 2-35; $Al_2O_3$: 2-15; CaO and/or MgO: 0-10; and $Na_2O$: 0-10.

Particularly preferred FAS fillers have the following composition (wt. %): $SiO_2$: 20-35; $Al_2O_3$: 15-35; BaO or SrO: 10-25; CaO: 0-20; ZnO: 0-15; $P_2O_5$: 5-20; $Na_2O$, $K_2O$, $Cs_2O$: 0-10 each; and $CaF_2$: 0.5-20. Particularly preferred are FAS fillers with the composition of (wt. %): $SiO_2$: 20-30; $Al_2O_3$: 20-30; BaO or SrO: 10-25; CaO: 5-20; $P_2O_5$: 5-20; $Na_2O$: 0-10; and $CaF_2$: 5-20.

All data refer to the total mass of the glass, with all components except fluorine being calculated as oxides, as is usual for glasses and glass ceramics.

The FAS fillers and radiopaque glass fillers preferably have an average particle size of 0.2 to 20 μm and particularly preferably of 0.4 to 5 μm.

The compositions according to the invention preferably contain from 25 to 80 wt. %, more preferably from 30 to 75 wt. %, and most preferably from 40 to 70 wt. % of FAS filler and/or radiopaque glass filler, in each case based on the total mass of the composition.

In addition to the aforementioned FAS and radiopaque glass fillers, the compositions according to the invention may contain further fillers.

Preferred further fillers are metal oxides, particularly preferably mixed oxides, containing 60 to 80 wt. % $SiO_2$ and at least one of the metal oxides $ZrO_2$, $Y_2bO_3$, ZnO, $Ta_2O_5$, $Nb_2O_5$ and/or $La_2O_3$, so that the total amount adds up to 100%. Mixed oxides such as $SiO_2$—$ZrO_2$ are accessible, for example, by hydrolytic co-condensation of metal alkoxides. The metal oxides preferably have an average particle size of 0.05 to 10 μm, particularly preferably of 0.1 to 5 μm.

Other preferred additional fillers are fumed silica or precipitated silica with a primary particle size of 0.01 to 0.15 μm, as well as quartz or glass ceramic powder with a particle size of 0.1 to 15 μm, preferably from 0.2 to 5 μm, and ytterbium trifluoride. The ytterbium trifluoride preferably has a particle size of 80 to 900 nm and particularly preferably of 100 to 300 nm.

In addition, so-called composite fillers are preferred as further fillers. These are also referred to as isofillers. These are splinter-like polymers which in turn contain a filler, preferably pyrogenic $SiO_2$ and/or ytterbium trifluoride as defined above. Preferred are polymers based on dimethacrylates. For the production of isofillers, the one or more fillers are incorporated, for example, into a dimethacrylate resin matrix, the resulting composite paste is subsequently thermally polymerized and then ground.

A composite filler preferred according to the invention can be prepared, for example, by thermally curing a mixture of bis-GMA (8.80 wt. %), UDMA (6.60 wt. %), 1,10-decanediol dimethacrylate (5.93 wt. %), dibenzoyl peroxide and 2,6-di-tert.-butyl-4-methylphenol (together 0.67 wt. %), glass filler (average grain size 0.4 μm; 53.0 wt. %) and $YbF_3$ (25.0 wt. %) before grinding the cured material to the desired grain size. All percentages refer to the total mass of the composite filler.

So-called inertized fillers can also be used as further fillers. These are glass fillers whose surface is coated with a diffusion barrier layer, e.g. on a sol-gel basis, or with a polymer layer, e.g. of PVC. Preferred fillers are those described in EP 2 103 296 A1 and corresponding U.S. Pat. No. 7,932,304 B2, which US patent is hereby incorporated by reference in its entirety.

To improve the bond between filler and matrix, the fillers are preferably surface modified with methacrylate-functionalized silanes, such as 3-methacryloyloxypropyltri-methoxysilane.

The compositions according to the invention preferably contain 0.1 to 25 wt. %, more preferably 1 to 20 wt. %, and most preferably 2 to 15 wt. % of one or more further fillers, preferably one or more metal oxides, fumed silica and/or precipitated silica, in each case based on the total mass of the composition.

The compositions according to the invention may also contain additional additives, in particular stabilizers, colorants, microbicidal agents, fluoride ion-releasing additives, such as fluoride salts, in particular NaF or ammonium fluoride, or fluorosilanes, optical brighteners, plasticizers, and/or UV absorbers.

Preferably, the compositions according to the invention comprise:

- 5 to 60 wt. %, preferably 8 to 45 wt. %, and particularly preferably 10 to 35 wt. % of at least one radically polymerizable monomer without an acid group,
- 1 to 15 wt. %, preferably 2 to 12 wt. %, and particularly preferably 3 to 10 wt. % of at least one acid group-containing, radically polymerizable monomer,
- 25 to 80 wt. %, preferably 30 to 75 wt. %, and particularly preferably 40 to 70 wt. % of at least one FAS filler and/or radiopaque glass filler,
- 0.1 to 8 wt. %, preferably 0.5 to 6 wt. %, and particularly preferably 1 to 5 wt. % of at least one initiator for radical polymerization, and
- 0.5 to 6.0 wt. %, preferably 0.7 to 5.0 wt. %, and particularly preferably 1.0 to 4.0 wt. % of at least one masking agent.

Unless otherwise stated, all percentages herein refer to the total mass of the composition. All amounts for radically polymerizable monomers (poly- and monofunctional) refer only to monomers without an acid group and do not include monomers containing an acid group.

The initiator can be a redox initiator, a photoinitiator, or an initiator for dual curing. The amounts mentioned include all initiator components, i. e. the initiators themselves and, if present, reducing agents, transition metal compound, etc. According to the invention, compositions containing at least one redox initiator or at least one redox initiator and at least one photoinitiator are preferred.

According to the invention, those compositions are particularly preferred which contain the following ingredients:

a) 0.5 up to 6 wt. %, preferably 0.7 to 5 wt. %, and particularly preferably 1.0 to 4.0 wt. % of at least one solid masking agent, b) 5 to 40 wt. %, preferably 8 to 30 wt. %, and particularly preferably 10 to 25 wt. % of at least one polyfunctional monomer without an acid group,
c) 1 to 15 wt. %, preferably 2 to 12 wt. %, and particularly preferably up 3 to 10 wt. % of at least one monomer containing an acid group,
d) 0 to 10 wt. %, preferably 0 to 8 wt. %, and particularly preferably 1 to 5 wt. % of one or more oligomeric carboxylic acids,
e) 1 to 20 wt. %, preferably 2 to 15 wt. %, and particularly preferably 3 to 10 wt. % of one or more monofunctional monomers without an acid group,
f) 25 to 80 wt. %, preferably 30 to 75 wt. %, and particularly preferably 40 to 70 wt. % of at least one FAS filler and/or radiopaque glass filler,
g) 0.1 up to 25 wt. %, preferably 1 to 20 wt. %, and particularly preferably 2 to 15 wt. % of one or more additional fillers,
h) 0.1 to 8 wt. %, preferably 0.5 to 6 wt. %, and particularly preferably 1 to 5 wt. % of an initiator for the radical polymerization,
i) 0 to 20 wt. %, preferably 0.2 to 10 wt. %, and particularly preferably 1 to 7 wt. % water, and
j) 0.001 to 5 wt. %, preferably 0.002 to 3 wt. %, and particularly preferably 0.005 to 2 wt. % of additives, in each case based on the total mass of the composition.

Compositions containing a redox initiator are also referred to as self-curing. They are preferably used in the form of two spatially separated components, i.e., as a 2-component system (2C system). Oxidizing and reducing agents are incorporated into separate components of the composition. One component, the so-called catalyst paste, contains the oxidizing agent, preferably a peroxide or hydroperoxide, and the second component, the so-called base paste, contains the corresponding reducing agent and optionally a photoinitiator and optionally catalytic amounts of a transition metal compound. Polymerization is initiated by mixing the components. Compositions containing both a redox initiator and a photoinitiator are referred to as dual-curing.

In two-component compositions, the masking agent is preferably added to the component containing the strongly acidic adhesive monomer, the FAS filler, and/or the radiopaque glass filler.

According to the invention, 2-component systems are preferred. They are preferably self-curing or dual-curing. The pastes are mixed together shortly before use, preferably with a double-push syringe.

The catalyst paste preferably has the following composition:

a) 1.0 to 12 wt. %, preferably 1.4 to 10 wt. %, and particularly preferably 2.0 to 8.0 wt. % of at least one solid masking agent,
b) 5 to 40 wt. %, preferably 8 to 30 wt. %, and particularly preferably 10 to 25 wt. % of at least one polyfunctional monomer without an acid group,
c) 2 to 30 wt. %, preferably 4 to 24 wt. %, and particularly preferably 6 to 20 wt. % of at least one monomer containing an acid group,
d) 0.1 to 20 wt. %, preferably up 1 to 16 wt. %, and particularly preferably 2 to 10 wt. % of one or more oligomeric carboxylic acids,
e) 1 to 20 wt. %, preferably 2 to 15 wt. %, and particularly preferably 3 to 10 wt. % of one or more monofunctional monomers without an acid group,
f) 25 to 80 wt. %, preferably 30 to 75 wt. %, and particularly preferably 40 to 70 wt. % of at least one FAS and/or glass filler,
g) 0.1 to 25 wt. %, preferably 1 to 20 wt. %, and particularly preferably 2 to 15 wt. % of one or more additional fillers,
h) 0.01 to 16 wt. %, preferably 0.02 to 12 wt. %, and particularly preferably 0.03 to 10 wt. % of at least one peroxide and/or hydroperoxide and optionally at least one photoinitiator,
i) 0 to 20 wt. %, preferably 0.2 to 10 wt. %, and particularly preferably 1 to 7 wt. % of water, and
j) 0.001 to 5 wt. %, preferably 0.002 to 3 wt. %, and particularly preferably 0.005 to 2 wt. % of additives, in each case based on the total mass of the catalyst paste.

The base paste preferably has the following composition:

a) not applicable,
b) 5 to 40 wt. %, preferably 8 to 30 wt. %, particularly preferably 10 to 25 wt. % of at least one polyfunctional monomer without an acid group,
c) not applicable,
d) not applicable,
e) 1 to 20 wt. %, preferably 2 to 15 wt. %, and particularly preferably 3 to 10 wt. % by weight of one or more monofunctional monomers without an acid group,
f) 25 to 80 wt. %, preferably 30 to 75 wt. %, and particularly preferably 40 to 70 wt. % of at least one fluoroaluminosilicate glass filler and/or glass filler,
g) 0.1 up to 25 wt. %, preferably 1 to 20 wt. %, and particularly preferably 2 to 15 wt. % of one or more additional fillers,
h) 0.01 to 16 wt. %, preferably 0.02 to 12 wt. %, and particularly preferably 0.03 to 10 wt. % of at least one suitable reducing agent and optionally a photoinitiator,
i) 0 to 20 wt %, preferably 0.2 to 10 wt. %, and particularly preferably 1 to 7 wt. % of water, and
j) 0.001 to 5 wt. %, preferably 0.002 to 3 wt. %, and particularly preferably 0.005 to 2 wt. % of additives, in each case based on the total mass of the base paste.

For application, the catalyst and base paste are preferably mixed together in approximately equal proportions. They are therefore particularly suitable for application with a double-push syringe.

Double-push syringes have two separate cylindrical chambers for holding base paste and catalyst paste. The components are pressed out of the chambers simultaneously by two interconnected pistons and are preferably forced through a mixing cannula and mixed together therein. For pressing out the pastes, the syringe can be inserted into a so-called hand dispenser, which facilitates handling of the syringes.

The compositions according to the invention are characterized by high storage stability and improved transparency, preferably greater than 10%, and good self-adhesion to enamel/dentin. They are particularly suitable as dental materials for intraoral use by the dentist for the restoration of damaged teeth (therapeutic use), especially as dental cements, coating materials or veneering materials, filling composites and most particularly as luting cements. The transparency is determined in the manner described in the examples.

For the treatment of damaged teeth, these are preferably prepared in a first step by the dentist. Subsequently, at least one composition according to the invention is applied to or into the prepared tooth. Thereafter, the composition can be cured directly, preferably by irradiation with light of a suitable wavelength, e. g. when restoring cavities. Alternatively, a dental restoration, for example an inlay, onlay, veneer, crown, bridge, framework, or dental ceramic, is placed in or applied to the prepared tooth. Subsequent curing of the composition is done preferably by light and/or self-curing. The dental restoration is attached to the tooth in this process.

The compositions according to the invention can also be used as extraoral materials (non-therapeutic), for example in the fabrication or repair of dental restorations. They are also suitable as materials for the fabrication and repair of inlays, onlays, crowns, or bridges.

For the production of dental restorations such as inlays, onlays, crowns, or bridges, at least one composition according to the invention is formed into the desired dental restoration in a manner known per se and then cured. The curing can be done by light, self-curing, or preferably thermally.

In the repair of dental restorations, the compositions according to the invention are placed onto the restoration to be repaired, e. g. to repair gaps or to bond fragments, and then cured.

The invention is explained in more detail below with reference to figures and examples.

FIG. 1 shows the decrease in concentration of the acidic monomer MDP as a function of storage time in composite pastes with (▼; ●) and without (■) EDTA.

Figure 2:
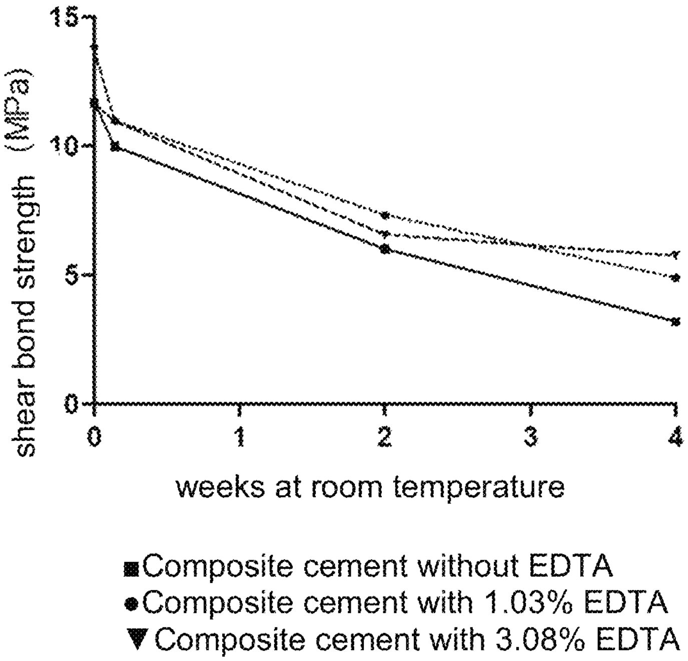
FIG. 2 shows a decrease in shear bond strength of composite cements with (▼; ●) and without (■) EDTA as a function of storage time.

FIG. 2 shows the decrease in shear bond strength of composite cements with (▼; ●) and without (■) EDTA as a function of storage time.

Example 1

Investigation of the Storage Stability of Self-Adhesive Composites With/Without EDTA.

Composite pastes C-1 to C-3 were prepared with the compositions given in Table 1 (all data in wt. %) from the following components: experimental radiopaque glass filler 1 (composition (wt. %): $Al_2O_3$: 6; $B_2O_3$: 5; $Na_2O$: 8; CaO, BaO, $K_2O$: each about 2-3; $CaF_2$; MgO each about 1; and $SiO_2$: 70; unsilanized), 10-methacryloyloxydecyl dihydrogen phosphate (MDP, Orgentis), triethylene glycol dimethacrylate (TEG-DMA), NK ester 9G (polyethylene glycol-400-dimethacrylate, Kowa Europa GmbH), V-392 (N,N'-diethyl-1,3-bis(acrylamido)-propane, Ivoclar Vivadent AG), BHT (2,6-di-tert-butyl-p-cresol): deionized water and ethylenediaminetetraacetic acid (EDTA, Aldrich).

TABLE 1

| Composition of composite pastes (wt. %) | | | |
|---|---|---|---|
| Component | C-1 *) (without EDTA) | C-2 | C-3 |
| TEGDMA | 11.28 | 10.86 | 11.13 |
| NK ester 9G | 2.38 | 2.29 | 2.35 |
| V-392 | 14.66 | 14.12 | 14.47 |
| MDP | 4.20 | 4.04 | 4.14 |
| BHT | 0.04 | 0.04 | 0.04 |
| Water | 6.99 | 6.74 | 6.91 |
| EDTA | 0 | 3.66 | 1.26 |
| Glass filler 1 | 60.45 | 58.25 | 59.70 |

*) comparative example

Pastes C-1 (without EDTA) and C-2 (3.66% EDTA) and C-3 (1.26% EDTA) were stored at room temperature and the content of MDP was determined by HPLC at intervals of several weeks. For HPLC measurement, an HPLC Ultimate 3000 instrument (ThermoFisher Scientific) with a 125×4 Nucleodur 100-5 C18ec column and a UV/VIS detector (220 nm) was used. The sample was dissolved in methanol and eluted with 0.01 mol/l $H_3PO_4$ in water (A), methanol (B) and acetonitrile (C) according to the following program. The results are shown in FIG. 1.

Gradient Program

| Time (min) | % A | % B | % C |
|---|---|---|---|
| 0 | 40% | 40% | 20% |
| 6 | 40% | 40% | 20% |
| 20 | 0% | 0% | 100% |
| 24 | 0% | 0% | 100% |

The results shown in FIG. 1. demonstrate a significantly improved storage stability of the composite pastes C-2 and C-3 with EDTA. Composite paste C-1 (■) without EDTA shows a significant decrease in available MDP already after 3-4 weeks, whereas in composite pastes C-2 (▼) and C-3 (●) with EDTA, more than ⅔ of the original MDP was still available after 24 weeks.

Example 2

Preparation of Dual-Curing Self-Adhesive Composite Cements

Analogous to Example 1, the catalyst pastes CP-1 (without EDTA), CP-2 and CP-3 (with EDTA) as well as the base paste were prepared with the compositions shown in Table 2. The dentin adhesion of the materials was determined as a function of storage time. For the investigation of dentin adhesion, bovine teeth were embedded in plastic cylinders in such a way that the dentin and the plastic were in one plane. After 15 s of etching with 37% phosphoric acid, they were thoroughly rinsed with water. The acid etching opened the dentin tubules. Then the catalyst pastes were mixed separately, each in a ratio of 1:1, with the base paste to form cements. A layer of the mixture to be tested was then applied to the tooth with a microbrush and exposed to a halogen lamp (Astralis 7, Ivoclar Vivadent AG) for 40 s. A composite cylinder made of a dental composite material (Tetric® Ceram; Ivoclar Vivadent AG) was polymerized onto the cement layer in two layers of 1-2 mm each, each of which was cured by 40 s exposure with the halogen lamp Astralis 7. The test specimens were then stored in water at 37° C. for 24 h and the shear bond strength was determined. The results are shown in FIG. 2.

With the cement based on the base paste and the paste CP-1 (■) without EDTA, a dentin bond strength value of 3.21 MPa was determined after 28 days. In contrast, the cements based on the base paste and the pastes with EDTA CP-2 (▼) and CP-3 (●), respectively, yielded significantly higher dentin bond strength values of 5.76 MPa (CP-2) and 4.42 MPa (CP-3) after 4 weeks of storage at room temperature.

TABLE 2

| Composition of the base and catalyst pastes (wt. %) | | | | |
|---|---|---|---|---|
| Component | CP-1*) | CP-2 | CP-3 | Base paste |
| MDP | 3.39 | 3.39 | 3.39 | — |
| TEGDMA | 10.66 | 10.66 | 10.66 | 8.81 |
| NK ester 9G | 2.37 | 2.37 | 2.37 | 2.59 |
| UDMA | 14.59 | 14.59 | 14.59 | 12.90 |
| Dibenzoyl peroxide (50%) | 0.960 | 0.960 | 0.960 | — |

TABLE 2-continued

Composition of the base and catalyst pastes (wt. %)

| Component | CP-1*) | CP-2 | CP-3 | Base paste |
|---|---|---|---|---|
| N,N-diethyl-3,5-di-tert•butyl-aniline | — | — | — | 1.00 |
| Camphorquinone | — | — | — | 0.078 |
| 4-(dimethylamino)-benzoic acid ethyl ester | — | — | — | 0.155 |
| BHT | 0.0312 | 0.0312 | 0.0312 | — |
| Inhibitor 1) | — | — | — | 0.00091 |
| EDTA | — | 3.08 | 1.03 | — |
| FAS filler (G018-056 1.0 μm, 5% silane.)2) | 67.00 | 63.92 | 65.97 | 3.07 |
| FAS filler (G018-056 7.0 μm, 5% silane.)3) | — | — | — | 69.70 |
| HDK 20004) | 1.00 | 1.00 | 1.00 | 1.49 |
| Benzyltributyl-ammonium chloride | — | — | — | 0.207 |
| Color pigment Lumilux LZ Flu Blue5) | — | — | — | 0.00085 |

*) comparative example

1) TEMPO: 2,2,6,6-tetramethylpiperidinyloxyl, CAS number 2564-83-2.

2) composition (wt. %): $Al_2O_3$: 24; $SiO_2$: 23; CaO: 16.5; $CaF_2$: 16; BaO: 11.5; $P_2O_5$: 8; $Na_2O$: 2; 5% silane; average particle diameter 1 μm (Schott AG, Mainz)

3) composition (wt. %): $Al_2O_3$: 24; $SiO_2$: 23; CaO: 16.5; $CaF_2$: 16; BaO: 11.5; $P_2O_5$: 8; $Na_2O$: 2; 5% silane; average particle diameter 7 μm (Schott AG, Mainz).

4) pyrogenic silica; trimethylsiloxy surface modification; BET surface area (DIN ISO 9277 DIN 66132) unsilanized: approx. 200 $m^2/g$; density ($SiO_2$; DIN 51757): 2.2 $g/cm^3$; residual silanol content (relative silanol content based on unsilanized silica with approx. 2 $SiOH/nm^2$): 25% (Wacker Chemie AG)

5) 2,5-dihydroxyterephthalic acid diethyl ester (Riedel-de Haën AG)

The transparency of the composite cements was measured in transmission by means of a spectrophotometer (Konika-Minolta Spectrophotometer CM-5) on 1 mm thick test specimens polished to high gloss. The transparency determination of the cements based on the base paste and catalyst pastes CP-1 to CP-3 gave the following transparency values: CP-1: 21.1%; CP-2: 16.7%, CP-3: 18.8%. Although the transparency of the cements based on catalyst pastes CP-2 and CP-3 was somewhat reduced by the addition of EDTA compared to the cement based on CP-1, the transparency values of the composite cements according to the invention are significantly higher than those of classical glass ionomer cements, such as Vivaglass CEM PL (Ivoclar Vivadent AG) with a transparency of 6.7%.

The invention claimed is:

1. A radically polymerizable composition comprising at least one acidic radically polymerizable monomer, at least one fluoroaluminosilicate glass filler, and/or radiopaque glass filler, and at least one masking agent, characterized in that the masking agent is in solid form and in that the composition comprises a catalyst paste as a first component and a base paste as a second component, wherein the masking agent is added in an amount of 1.0 to 12 wt. %, based on the total mass of the paste, to the paste containing the acidic radically polymerizable monomer and the fluoroaluminosilicate glass filler and/or radiopaque glass filler.

2. The composition according to claim 1, wherein the masking agent comprises ethylenediaminetetraacetic acid (EDTA) and its disodium salt (disodium ethylenediaminetetraacetate), nitrilotriacetic acid, diethy-lenetriaminepentaacetic acid, tetrasodium iminodisuccinate, and the trisodium salt of methylglycinediacetic acid.

3. The composition according to claim 1, wherein the masking agent is in particulate form and has a volume average particle size (D50 value) in a range selected from 300 to 350 μm, 200 to 250 μm, and 100 to 170 μm, and also has a D10 value in a range selected from 130 to 150 μm, 80 to 100 μm, and 70 to 55 μm.

4. The composition according to claim 1, which comprises 5 to 60 wt. % of at least one radically polymerizable monomer without an acid group, 1 to 15 wt. % of at least one radically polymerizable monomer containing an acid group, 25 to 80 wt. % of at least one fluoroaluminosilicate glass filler and/or radiopaque glass filler, 0.1 to 8 wt. % of at least one initiator for radical polymerization, and 0.5 to 6.0 wt. % of at least one masking agent, in each case based on the total mass of the composition.

5. The composition according to claim 4, which comprises a) 0.5 to 6 wt. % of at least one solid masking agent, b) 5 to 40 wt. % of at least one polyfunctional monomer without an acid group, c) 1 to 15 wt. % of at least one monomer containing an acid group, d) 0 to 10 wt. % of one or more oligomeric carboxylic acids, e) 1 to 20 wt. % of one or more monofunctional monomers without an acid group, f) 25 to 80 wt. % of at least one fluoroaluminosilicate glass filler and/or radiopaque glass filler, g) 0.1 to 25 wt. % of one or more additional fillers, h) 0.1 to 8 wt. % of an initiator for radical polymerization, i) 0 to 20 wt. % of water, and j) 0.001 to 5 wt. % of additives, in each case based on the total mass of the composition.

6. The composition according to claim 5, wherein the polyfunctional monomer (b) comprises at least one monomer selected from bisphenol A dimethacrylate, bis-GMA (an addition product of methacrylic acid and bisphenol A diglycidyl ether), ethoxy- or propoxylated bisphenol A dimethacrylates, urethanes of 2-(hydroxymethyl)acrylic acid and diisocyanates, UDMA (an addition product of 2hydroxyethyl methacrylate and 2,2,4-trimethylhexamethylene,1,6-diisocyanate),tetramethylxylylene diurethane ethylene glycol di(meth)acrylate or tetramethylxylylene diurethane-2-methylethylene glycol diurethane di(meth)acrylate (V380), di-, tri-or tetraethylene glycol dimethacrylate, trimethylolpropane trimethacrylate, pentaerythritol tetramethacrylate, glycerol di-methacrylate, glycerol trimethacrylate, 1,4-butanediol dimethacrylate, 1,10-decanediol dimethacrylate ($D_3MA$), bis(methacryloyloxymethyl)tricyclo-[5.2.1.0$^{2,6}$]decane (DCP), polyethylene glycol dimethacrylates, polypropylene glycol dimethacrylates, 1,12-dodecanediol dimethacrylate, radically polymerizable pyrrolidones, bisacrylamides, bis(meth)acrylamides, and mixtures thereof.

7. The composition according to claim 5, wherein the at least one monomer containing an acid group (c) comprises at least one monomer selected from monomers containing a phosphoric ester group or phosphonic acid group,.

8. The composition according to claim 5, wherein the oligomeric carboxylic acid (d) comprises polyacrylic acid with a number average molecular weight less than 7,200 g/mol.

9. The composition according to claim 5, wherein the monofunctional monomer (e) comprises at least one monomer selected from benzyl (meth)acrylate, tetrahydrofurfuryl (meth)acrylate, isobornyl (meth)acrylate, p-cumyl phenoxyethylene glycol methacrylate (CMP-1E), 2-([1,1'-biphenyl]-2-oxy)ethyl methacrylate (MA-836), tricyclodecane methyl (meth) acrylate, 2-(2-biphenyloxy)ethyl (meth)acrylate, 2-hydroxyethyl (methacrylate), hydroxyethylpropyl (methacrylate), 2-acetoxyethyl methacrylate, and mixtures thereof.

10. The composition according to claim 4, wherein the a radiopaque glass filler comprises the composition (wt. %): $SiO_2$: 20-80; $B_2O_3$: 2-15, BaO or SrO: 0-40; $Al_2O_3$: 2-20; CaO and/or MgO: 0-20; $Na_2O$, $K_2O$, $Cs_2O$: 0-10 each; $WO_3$: 0-20; ZnO: 0-20; $La_2O_3$: 0-10; $ZrO_2$: 0-15; $P_2O_5$: 0-30; $Ta_2O_5$, $Nb_2O_5$ or $Yb_2O_3$: 0-5; and $CaF_2$ and/or $SrF_2$ 0-10; and/or wherein the fluoroaluminosilicate glass filler comprises the composition (wt. %): $SiO_2$: 20-35; $Al_2O_3$: 15-35; BaO or SrO: 10-25; CaO: 0-20; ZnO: 0-15; $P_2O_5$: 5-20; $Na_2O$, $K_2O$, $Cs_2O$: 0-10 each; and $CaF_2$: 0.5-20 wt. %; with all figures being based on the total mass of the glass and all components except fluorine being calculated as oxides.

11. The composition according to claim 1, comprising at least one redox initiator or at least one redox initiator and at least one photoinitiator.

12. The composition according to claim 1, wherein the catalyst paste comprises a) 1.0 to 12 wt. % of at least one solid masking agent, b) 5 to 40 wt. % of at least one polyfunctional monomer without an acid group, c) 2 to 30 wt. % of at least one monomer containing an acid group, d) 0.1 to 20 wt. % of one or more oligomeric carboxylic acids, e) 1 to 20 wt. % of one or more monofunctional monomers without an acid group, f) 25 to 80 wt. % of at least one fluoroaluminosilicate glass filler and/or glass filler, g) 0.1 to 25 wt. % of one or more additional fillers, h) 0.01 to 16 wt. % of at least one peroxide and/or hydroperoxide and optionally at least one photoinitiator, i) 0 to 20 wt. % of water, and j) 0.001 to 5 wt. % of additives, in each case based on the total mass of the catalyst paste, and wherein the base paste comprises a) not applicable, b) 5 to 40 wt. % of at least one polyfunctional monomer without an acid group, c) not applicable, d) not applicable, e) 1 to 20 wt. % of one or more monofunctional monomers without an acid group, f) 25 to 80 wt. % of at least one fluoroaluminosilicate glass filler and/or glass filler, g) 0.1 to 25 wt. % of one or more additional fillers, h) 0.01 to 16 wt. % of at least one suitable reducing agent and optionally a photoinitiator, i) 0 to 20 wt. % of water, and j) 0.001 to 5 wt. % of additives, in each case based on the total mass of the base paste.

13. The composition of claim 12, wherein the catalyst paste and the base paste are each contained in different chambers of a dual-push syringe.

14. The composition according to claim 1 for therapeutic use as a dental material comprising a dental cement, coating or veneering material, restorative composite or luting cement.

15. The composition according to claim 1 for non-therapeutic use for the manufacture or repair of dental restorations comprising inlays, onlays, crowns or bridges.

16. The composition according to claim 6, wherein the at least one ethoxy- or propoxylated bisphenol A dimethacrylate is selected from bisphenol A dimethacrylate with 3 ethoxy groups or 2,2-bis [4-(2-methacry-loyloxypropoxy)phenyl]propane, and/or wherein the diisocyanate of the at least one urethane of 2-(hydroxymethyl)acrylic acid and diisocyanate is selected from 2,2,4-trimethylhexamethylene diisocyanate or isophorone diisocyanate, and/or wherein the at least one radically polymerizable pyrrolidone is 1,6-bis(3-vinyl-2-pyrrolidonyl)-hexane, and/or wherein the at least one bisacrylamide is selected from methylene or ethylene bisacrylamide, and/or wherein the at least one bis(meth)acrylamide is selected from N,N'-diethyl-1,3-bis(acrylamido)propane, 1,3-bis (methacrylamido)propane, 1,4-bis(acrylamido)butane or 1,4-bis(acryloyl)piperazine.

17. The composition according to claim 7, wherein the at least one monomer containing a phosphoric ester group or phosphonic acid group is selected from 2-methacryloyloxyethylphenyl hydrogen phosphate, 10-methacryloyloxydecyl dihydrogen phosphate (MDP), glycerol dimethacrylate dihydrogen phosphate, dipentaerythritol pentamethacryloyloxy phosphate, 4-vinylbenzylphosphonic acid, 2-[4-(dihydroxyphosphoryl)-2-oxa-butyl]-acrylic acid and/or 2-[4-(dihydroxyphosphoryl)-2-oxa-butyl]-acrylic acid-2,4,6-trimethylphenyl ester, and/or wherein the at least one monomer containing a carboxy group is selected from 4-(meth)acryloyloxyethyltrimellitic anhydride, 10-methacryloyloxydecylmalonic acid, N-(2-hydroxy3-methacryloyloxypropyl)-N-phenylglycine and/or 4-vinylbenzoic acid.

* * * * *